US008249215B2

(12) United States Patent
Vaitheeswaran et al.

(10) Patent No.: US 8,249,215 B2
(45) Date of Patent: Aug. 21, 2012

(54) MIXED-ENERGY INTENSITY-MODULATED RADIATION THERAPY

(75) Inventors: Ranganathan Vaitheeswaran, Pune (IN); Vatyam Sathiya Narayanan, Pune (IN)

(73) Assignee: Siemens Medical Solutions USA, Inc., Malvern, PA (US)

( * ) Notice: Subject to any disclaimer, the term of this patent is extended or adjusted under 35 U.S.C. 154(b) by 309 days.

(21) Appl. No.: 12/616,006

(22) Filed: Nov. 10, 2009

(65) Prior Publication Data

US 2011/0110491 A1    May 12, 2011

(51) Int. Cl.
*A61N 5/10* (2006.01)
(52) U.S. Cl. ......................................... 378/65
(58) Field of Classification Search ............. 378/65
See application file for complete search history.

(56) References Cited

U.S. PATENT DOCUMENTS

| | | | | | |
|---|---|---|---|---|---|
| 5,458,125 | A * | 10/1995 | Schweikard | ............ | 600/407 |
| 5,663,999 | A * | 9/1997 | Siochi | ............ | 378/65 |
| 5,818,902 | A * | 10/1998 | Yu | ............ | 378/65 |
| 6,134,296 | A * | 10/2000 | Siochi | ............ | 378/65 |
| 6,459,762 | B1 * | 10/2002 | Wong et al. | ............ | 378/65 |
| 6,477,229 | B1 * | 11/2002 | Grosser | ............ | 378/65 |
| 6,487,274 | B2 * | 11/2002 | Bertsche | ............ | 378/143 |
| 6,493,424 | B2 * | 12/2002 | Whitham | ............ | 378/137 |
| 6,735,277 | B2 * | 5/2004 | McNutt et al. | ............ | 378/65 |
| 6,757,355 | B1 * | 6/2004 | Siochi | ............ | 378/65 |
| 6,853,705 | B2 * | 2/2005 | Chang | ............ | 378/65 |
| 6,882,702 | B2 * | 4/2005 | Luo | ............ | 378/65 |
| 6,907,105 | B2 * | 6/2005 | Otto | ............ | 378/65 |
| 7,283,611 | B1 * | 10/2007 | Luan et al. | ............ | 378/65 |
| 7,496,173 | B2 * | 2/2009 | Goldman et al. | ............ | 378/65 |
| 7,529,339 | B2 * | 5/2009 | Goldman et al. | ............ | 378/65 |

FOREIGN PATENT DOCUMENTS

EP    0 314 231    5/1989

OTHER PUBLICATIONS

T. Wiezorek, et al. *Experimental determination of peripheral doses for different IMRT techniques delivered by a Siemens linear accelerator* Strahlentherapie and Onkologie, vol. 184, No. 2, Feb. 1, 2008, pp. 73-79, XP002624850.

Bhangle Jr, et al., *Dose linearity and uniformity of Siemens ONCOR impression plus linear accelerator designed for step-and-shoot intensity-modulated radiation therapy*, Journal of Medical Physics, vol. 32, Jan. 1, 2007, pp. 103-107, XP009145137.

Grimes, *Solving Systems of Large Dense Linear Equations*, The Journal of Supercomputing, vol. 1, Apr. 19, 2007, pp. 291-299, XP002624853.

(Continued)

*Primary Examiner* — Allen C. Ho (57) ABSTRACT

A system includes determination of a plurality of radiation beams for a radiation treatment fraction, each of the plurality of beams associated with a respective intensity, beam aperture and beam energy, and at least two of the plurality of beams respectively associated with two different beam energies, and determination of a forward dose associated with the plurality of input beams. If it is determined that the forward dose does not conform to a dose prescription, a beam weight is determined for each of the plurality of input beams based on the forward dose and the dose prescription using Gaussian elimination, and a second forward dose associated with the plurality of input beams and their respective beam weights is determined.

10 Claims, 6 Drawing Sheets

OTHER PUBLICATIONS

Chawla, M M et al., *A fast parallel algorithm for the solution of tridiagonal linear systems*, International Journal of Computer Mathematics, Gordon and Breach Publishers, London GB, vol. 45, No. 1, Jan. 1, 1992, pp. 113-121, XP009145139, ISSN: 0020-7160.

Deshpande Shrikant, et al., *Dosimetric and QA aspects of Konrad inverse planning system for commissioning intensity-modulated radiation therapy*, Journal of Medical Physics/Association of Medical Physicists of India, vol. 32, No. 2, Apr. 1, 2007, pp. 51-55, XP009145138.

EP Search Report dated Mar. 23, 2011, in corresponding EP patent application No. EP10 19 0630, 8 pages total.

Martin, et al., "Accelerating IMRT Optimization by Voxel Sampling", Physics in Medicine and Biology, vol. 52, 2007, doi:10.1088/0031-9155/52/24/002, pp. 7211-7228 (18 pages total).

Bednarz, et al., "The Use of Mixed-Integer Programming for Inverse Treatment Planning with Pre-defined Field Segments", Physics in Medicine and Biology, vol. 47, 2002, PII:S0031-9155(02)36001-9, pp. 2235-2245 (11 pages total).

Knöös, et al., "Comparision of Dose Calculation Algorithms for Treatment Planning in External Photon Beam Therapy for Clinical Situations", Physics in Medicine and Biology, vol. 51, 2006, doi:10.1088/0031-9155/51/22/005, pp. 5785-5807 (23 pages total).

Webb, S., "Optimization by Simulated Annealing of Three-Dimensional Conformal Treatment Planning for Radiation Fields Defined by a Multileaf Collimator", Physics in Medicine and Biology, vol. 36, No. 9, 1991, pp. 1201-1226 (26 pages total).

Webb, S., "Optimization of Conformal Radiotherapy Dose Distributions by Simulated Annealing", Physics in Medicine and Biology, vol. 34, No. 10, 1989, pp. 1349-1370 (22 pages total).

Bedford, James L., "Speed Versus Accuracy in a Fast Convolution Photon Dose Calculation for Conformal Radiotherapy", Physics in Medicine and Biology, vol. 47, 2002, PII:S0031-9155(02)37947-8, pp. 3475-3484 (10 pages total).

Bortfield, et al., "Methods of Image Reconstruction from Projections Applied to Conformation Radiotherapy", Physics in Medicine and Biology, vol. 35, No. 10, 1990, pp. 1423-1434 (12 pages total).

Niemierko, et al., "Random Sampling for Evaluating Treatment Plans", Div. of Radiation Biophysics, Dept. of Radiation Medicine, Jun. 15, 1990, pp. 753-762 (10 pages total).

Rowbottom, et al., "Simultaneous Optimization of Beam Orientations and Beam Weighs in Conformal Radiotherapy", Medical Physics, vol. 28, No. 8, Aug. 2001, pp. 1696-1702 (7 pages total).

Starkschall, George, "A Constrained Least-Squares Optimization Method for External Beam Radiation Therapy Treatment Planning", Medical Physics, vol. 11, 1984, pp. 659-665 (7 pages total).

Xing, Lei, et al., "A Three-Dimensional Algorithm for Optimizing Beam Weights and Wedge Filters", Medical Physics, vol. 25, No. 10, Oct. 1998, pp. 1858-1865 (8 pages total).

Mohan, R., et al., "Clinically Relevant Optimization of 3-D Conformal Treatments", Medical Physics, vol. 19, 1992, pp. 933-944 (12 pages total).

Xiao, Y., et al., "An Optimized Forward-Planning Technique for Intensity Modulated Radiation Therapy", Medical Physics, vol. 27, No. 9, Sep. 2000, pp. 2093-2099 (7 pages total).

* cited by examiner

MIXED-ENERGY INTENSITY-MODULATED RADIATION THERAPY

BACKGROUND

1. Field

The embodiments described below relate generally to the delivery of therapeutic radiation to a patient. More specifically, some embodiments are directed to the delivery of intensity-modulated radiation therapy.

2. Description

According to conventional radiation therapy, a beam of radiation is directed toward a tumor located within a patient. The radiation beam delivers a predetermined dose of therapeutic radiation to the tumor according to an established treatment plan. The delivered radiation kills cells of the tumor by causing ionizations within the cells.

Treatment plans are therefore designed to maximize radiation delivered to a target while minimizing radiation delivered to healthy tissue surrounding the target. Intensity-modulated radiation therapy (IMRT) can often deliver radiation doses that conform tightly to a target volume. In particular, conventional IMRT systems can provide fine control over a delivered dose distribution by manipulating the number, intensity, and point of entry of radiation beams which comprise an IMRT fraction.

In some scenarios, sensitive healthy tissues are located proximate to a target in a manner that prevents conventional IMRT systems from delivering an otherwise desired dose to the target without subjecting the healthy tissues to an undesirable dose. What is needed is a system to efficiently determine and/or deliver IMRT to a target volume with a more flexible dose distribution than conventionally available.

SUMMARY

To address at least the foregoing, some embodiments provide a system, method, apparatus, and means to determine a plurality of radiation beams for a radiation treatment fraction, each of the plurality of beams associated with a respective intensity, beam aperture and beam energy, and at least two of the plurality of beams respectively associated with two different beam energies, and to determine a forward dose associated with the plurality of input beams.

In some aspects, if it is determined that the forward dose does not conform to a dose prescription, a beam weight is determined for each of the plurality of input beams based on the forward dose and the dose prescription using Gaussian elimination, and a second forward dose associated with the plurality of input beams and their respective beam weights is determined.

Embodiments may also or alternatively include a linear accelerator to deliver a plurality of input beams to a patient volume in a single treatment fraction, wherein each of the plurality of input beams is associated with a respective intensity, beam aperture and beam energy, and wherein at least two of the plurality of beams are respectively associated with two different beam energies. The linear accelerator may deliver one of the at least two of the plurality of beams of the single treatment fraction at a first beam energy, and deliver a second one of the at least two of the plurality of beams at a second beam energy.

The claims are not limited to the disclosed embodiments, however, as those in the art can readily adapt the description herein to create other embodiments and applications.

BRIEF DESCRIPTION OF THE DRAWINGS

The construction and usage of embodiments will become readily apparent from consideration of the following specification as illustrated in the accompanying drawings, in which like reference numerals designate like parts, and wherein.

DETAILED DESCRIPTION

The following description is provided to enable any person in the art to make and use the described embodiments and sets forth the best mode contemplated for carrying out the described embodiments. Various modifications, however, will remain readily apparent to those in the art.

Figure 1:
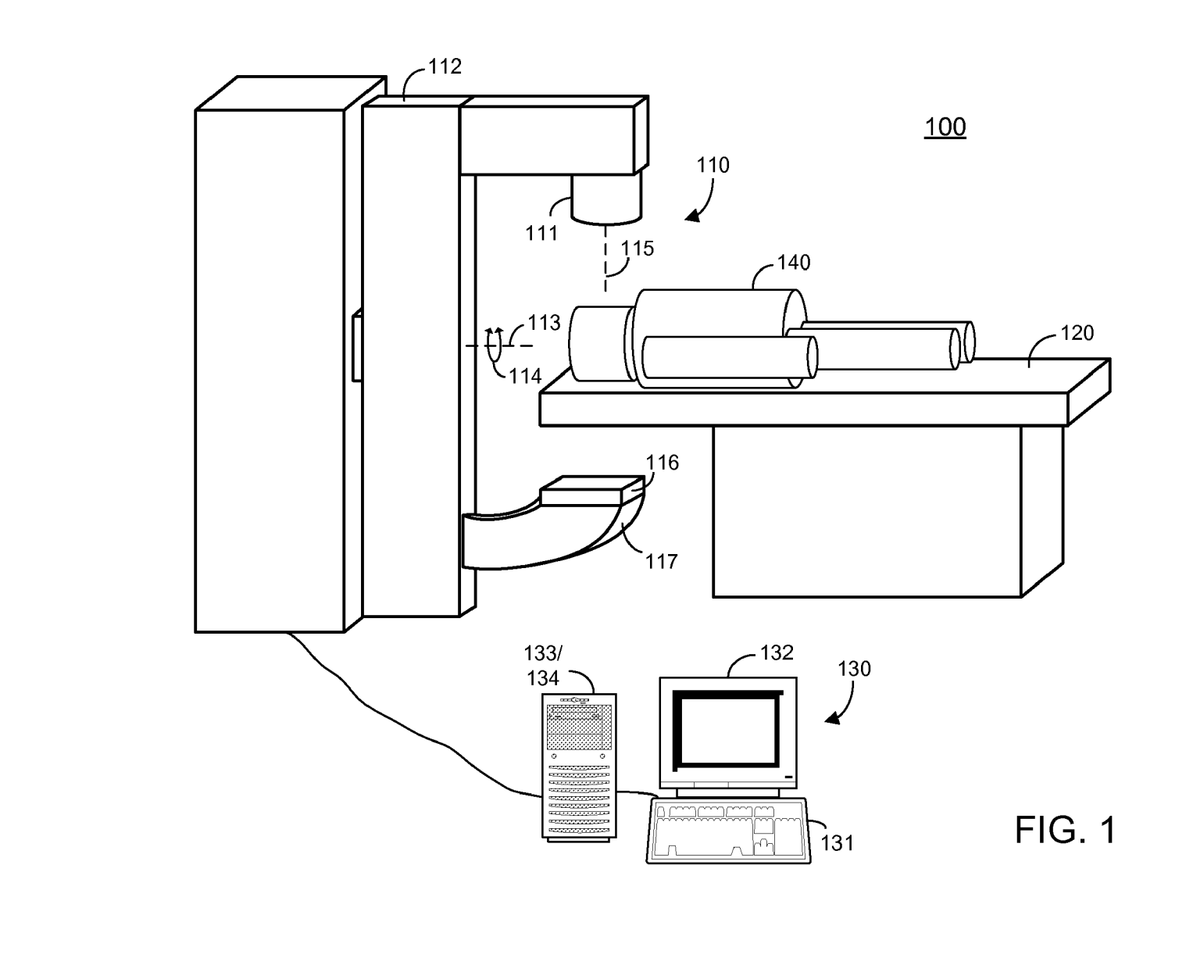
FIG. 1 is a perspective view of a radiation treatment room according to some embodiments.

FIG. 1 illustrates radiation treatment room 100 pursuant to some embodiments. Radiation treatment room 100 includes linear accelerator (linac) 110, table 120 and operator console 130. The elements of radiation treatment room 100 may be used to deliver radiation to a target volume of beam object 140. In this regard, beam object 140 may comprise a patient positioned to receive radiation according to a radiation treatment plan.

Linac 110 generates and emits the radiation, and is primarily composed of treatment head 111 and gantry 112. Treatment head 111 includes a beam-emitting device (not shown) for emitting one or more radiation beams during treatment, calibration, and/or other scenarios. An emitted radiation beam may comprise electron, photon or any other type of radiation. According to some embodiments, the radiation beam exhibits energies in the megavoltage range (i.e. >1 MV) and may therefore be referred to as megavoltage radiation. Also included within treatment head 111 is a beam-shielding device, or collimator (not shown) for shaping the beam and for shielding sensitive surfaces from the beam.

Treatment head 111 is coupled to a projection of gantry 112. Gantry 112 is rotatable around gantry axis 113 before, during and after radiation treatment. As indicated by arrow 114, gantry 112 may rotate clockwise or counter-clockwise according to some embodiments. Rotation of gantry 112 serves to rotate treatment head 111 around axis 113.

During radiation treatment, a radiation beam is emitted from treatment head 111 as a divergent beam. The beam is emitted towards an isocenter of linac 110. The isocenter is located at the intersection of beam axis 115 and gantry axis 113. Due to divergence of the radiation beam and the shaping of the beam by the aforementioned beam-shaping devices, the beam may deliver radiation to a volume of beam object 140 rather than only to the isocenter.

Table 120 supports beam object 140 during radiation treatment. Table 120 may be adjustable to assist in positioning a treatment area of beam object 140 at the isocenter of linac 110. Table 120 may also be used to support devices used for such positioning, for calibration and/or for verification.

Imaging device 116 may acquire images before, during and/or after radiation treatment. For example, imaging device 116 may be used to acquire images for verification and recordation of a target volume position and of an internal patient portal to which radiation is delivered.

Imaging device 116 may be attached to gantry 112 in any manner, including via extendible and retractable housing 117. Rotation of gantry 112 may cause treatment head 111 and imaging device 116 to rotate around the isocenter such that isocenter remains located between treatment head 111 and imaging device 116 during the rotation.

Imaging device 116 may comprise any system to acquire an image based on received megavoltage photon radiation. In a case that linac 110 is capable of producing kilovoltage photon radiation via beamline modification or other techniques, imaging device 116 may also acquire images based on such kilovoltage radiation. In some embodiments, imaging device 116 is a flat-panel imaging device using a scintillator layer and solid-state amorphous silicon photodiodes deployed in a two-dimensional array. In operation, the scintillator layer receives photons and generates light in proportion to the intensity of the received photons. The array of photodiodes receives the light and records the intensity of received light as stored electrical charge.

In other embodiments, imaging device 116 converts received photons to electrical charge without requiring a scintillator layer. The photons are absorbed directly by an array of amorphous selenium photoconductors. The photoconductors convert the photons directly to stored electrical charge. Imaging device 116 may also comprise a CCD or tube-based camera. Such an imaging device may include a light-proof housing within which are disposed a scintillator, a mirror, and a camera.

The charge developed and stored by imaging device 116 represents radiation intensities at each location of a radiation field produced by a beam emitted from treatment head 111. Since object 140 is located between treatment head and imaging device 116, the radiation intensity at a particular location represents the attenuative properties of tissues along a divergent line between a radiation source in treatment head 111 and the particular location. The set of radiation intensities acquired by imaging device 116 may therefore comprise a two-dimensional projection image of these tissues.

Operator console 130 includes input device 131 for receiving instructions from an operator and output device 132, which may be a monitor for presenting operational parameters of linac 110 and imaging device 116 and/or interfaces for receiving instructions. Output device 132 may also present a two-dimensional projection image, a three-dimensional megavoltage (or kilovoltage) cone beam image and/or two-dimensional "slice" images based on the three-dimensional image.

Input device 131 and output device 132 are coupled to processor 133 and storage 134. Processor 133 may execute program code to perform any of the determinations and generations described herein, and/or to cause linac 110 to perform any of the process steps described herein.

Storage 134 may also store program code to generate and/or modify a treatment plan according to some embodiments. Such code may comprise the SyngoRT™ suite or the KONRAD™ treatment planning system sold by Siemens Medical Solutions. Accordingly, storage 134 may also store radiation treatment plans in accordance with any currently- or hereafter-known format. The treatment plans may comprise scripts that are automatically executable by elements of room 100 to provide radiation therapy fractions. Each fraction of each treatment plan may require a patient to be positioned in a particular manner with respect to treatment head 111.

Operator console 130 may be in a room other than treatment room 100, in order to protect its operator from radiation. For example, treatment room 100 may be heavily shielded, such as a concrete vault, to shield the operator from radiation generated by linac 110.

Linac 110 may be operated so that each emitted beam exhibits a desired intensity (e.g., represented in monitor units (MU)) and aperture (i.e., a cross-sectional shape determined at least in part by the above-mentioned collimator), and is delivered from a desired gantry angle. The intensity, aperture and gantry angle of a beam are commonly specified by a treatment plan, and control software may configure linac 110 to automatically execute such a treatment plan by automatically delivering beams of the desired intensities and shapes from the desired angles.

In addition to the foregoing characteristics, each beam may exhibit one of a plurality of beam energies provided by linac 110. For example, linac 110 may be capable of selectively delivering a 6 MV radiation beam or a 15 MV radiation beam, although embodiments are not limited to these two energies. Accordingly, each radiation beam delivered by linac 100 may be associated with an intensity, an aperture, an angle and one of two or more available energies. By delivering beams of different energies, an additional degree of freedom is provided to facilitate delivery of a desired dose. In addition, the delivery of beams of different energies during a single IMRT treatment fraction can increase the effectiveness of IMRT.

In some embodiments, linac 110 includes features allowing rapid switching between two or more beam energies. The Siemens ONCOR Impression Plus linear accelerator includes an Auto Field Sequencer for switching between beam energies and may be suitable for use in conjunction with some embodiments.

Figure 2:
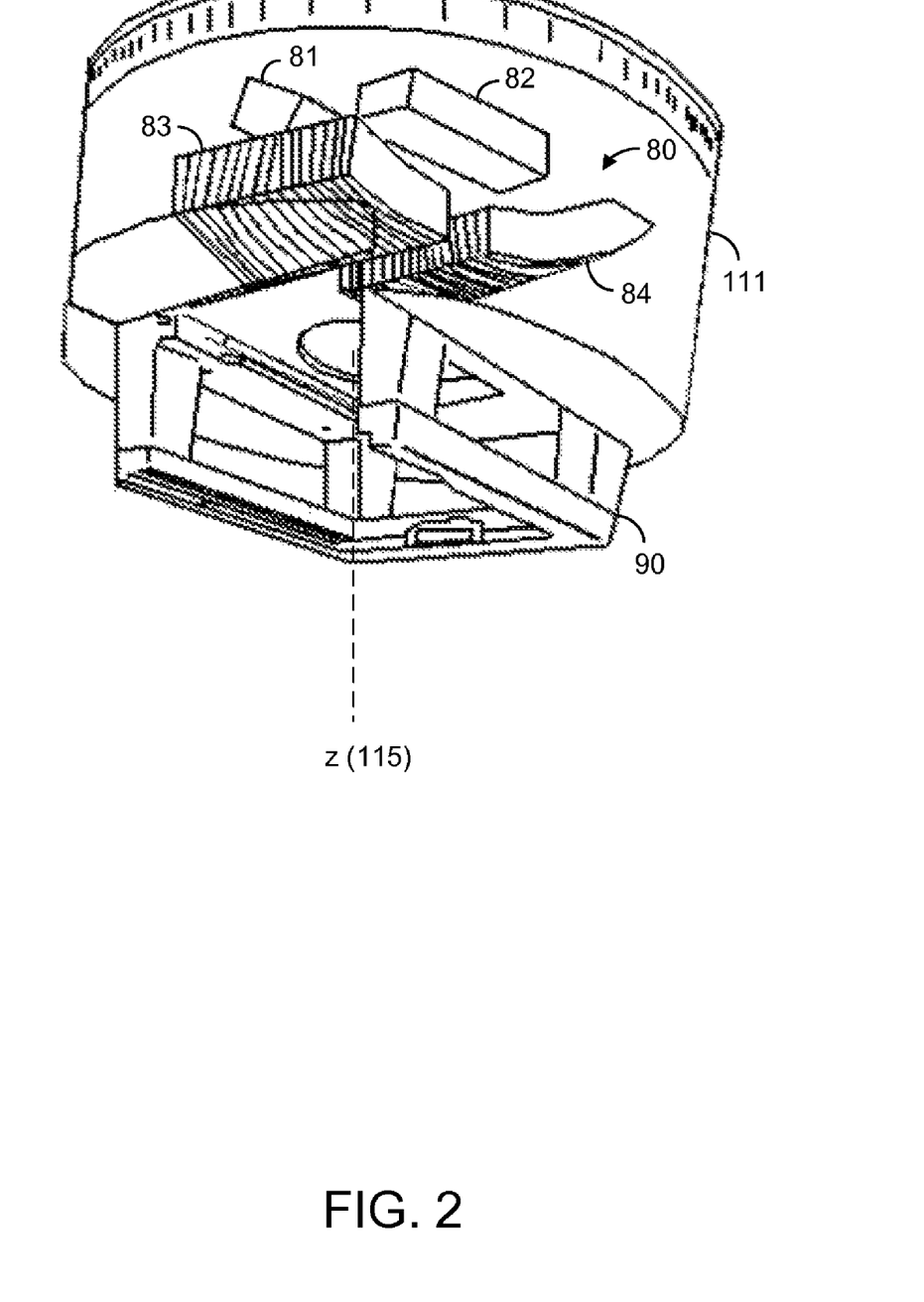
FIG. 2 is a transparent perspective view of a treatment head according to some embodiments.

FIG. 2 illustrates treatment head 111 according to some embodiments. Treatment head 111 includes collimator 80 that may be used to shape a radiation beam to conform to an aperture specified by a treatment plan. Collimator 80 includes a pair of jaws (Y-jaws) 81 and 82 and a pair of jaws (X-jaws) 83 and 84. The positioning of X-jaws 83 and 84 and Y-jaws 81 and 82 determines a size and shape of an opening through which a radiation beam may pass along axis 115.

Each pair of jaws 83/84 and 81/82 is rotatable about axis 115. As depicted in FIG. 2, X-jaws 83 and 84 may be formed of a plurality of individual elements. These individual elements may be movable along a path intersecting axis 115. Movement of each element may be individually controllable to generate a wide variety of aperture shapes.

Treatment head 111 also includes accessory tray 90. Accessory tray 90 may be configured to receive and securely hold attachments used during the course of treatment planning and treatment (such as, for example, reticles, wedges, or the like). According to some embodiments, treatment head 111 is rotatable to rotate collimator 80 and accessory tray 90 around axis 115 without disturbing the maintaining the physical relationships between X-jaws 83 and 84, Y-jaws 81 and 82, and accessory tray 90.

Figure 3:
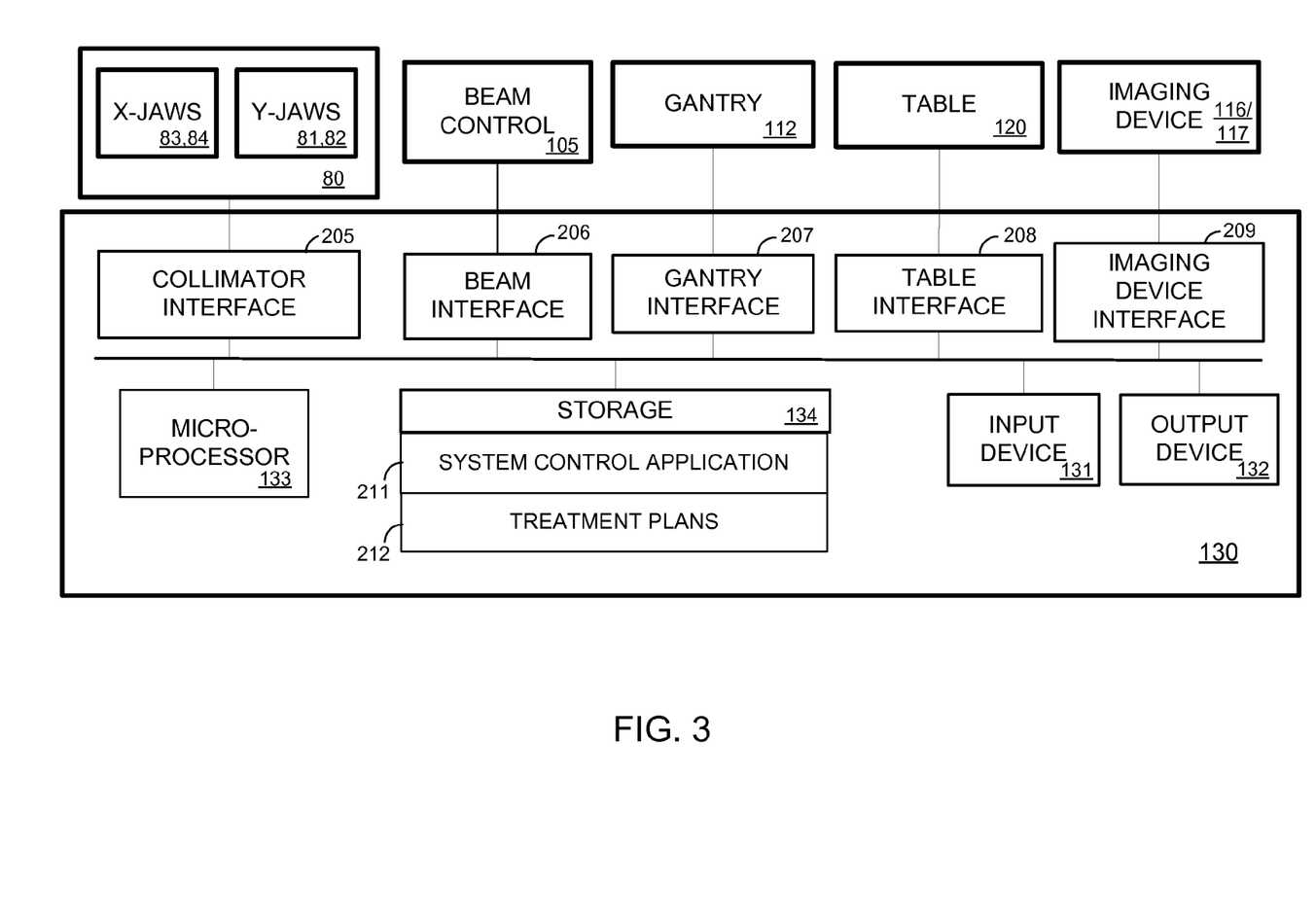
FIG. 3 is a block diagram of the internal architecture of radiation treatment room devices according to some embodiments.

FIG. 3 is a block diagram of elements of treatment room 100 according to some embodiments. The illustrated elements may be implemented by any suitable combination of hardware, software and/or firmware. Operator console 130 may be implemented by one or more separate computing systems.

As shown, operator console 130 includes several elements for interfacing with other elements of treatment room 100. Specifically, operator console 130 includes collimator interface 205, beam interface 206, gantry interface 207, table interface 208, and imaging device interface 209. Each of the interfaces may comprise any suitable type of hardware and/or software interface, and may or may not be proprietary. Operator console 130 may control the various elements through the interfaces and based on instructions from processor 133.

Collimator interface 205 may be used to control the opening and closing of each of jaws 81 through 84, the independent rotation of each pair of jaws, and/or the rotation of collimator 80. Beam interface 206 may control beam-controlling elements 105 of linac 110 based on desired beam characteristics. In particular, beam interface 206 may control trigger signals for controlling an injector current and RF power signal to generate a radiation beam having a particular energy.

Interfaces 205 through 209 may comprise dedicated hardware and/or software interfaces, and one or more of interfaces 205 through 209 may be implemented by a single interface. For example, interfaces 205 through 207 may be implemented by a single Ethernet interface and interfaces 208 and 209 may be implemented by proprietary interfaces for interfacing with table 120 and imaging device 116.

Microprocessor 133 executes processor-executable process steps stored in storage 134 to provide operation according to some embodiments. These process steps may comprise system control application 211 to execute one of treatment plans 212. System control application 211 may also comprise program code to generate and/or modify one or more of treatment plans 212 as described below. A separate computer system executing the same or other software may generate a treatment plan as described below in some embodiments. System control application 211 may also, in some embodiments, be used to calibrate imaging device 116, and to acquire projection images for verifying patient position.

Treatment plans 212 may conform to any currently- or hereafter-known format. Treatment plans 212 may comprise scripts that are automatically executable by linear accelerator 110 and treatment table 120 to provide radiation therapy fractions. Each of treatment plans 212 may require a patient to be positioned in a particular manner with respect to treatment head 111.

A hardware environment according to some embodiments may include less or more elements than those shown in FIGS. 1 through 3. In addition, embodiments are not limited to the illustrated devices and/or to the illustrated environment.

Figure 4:
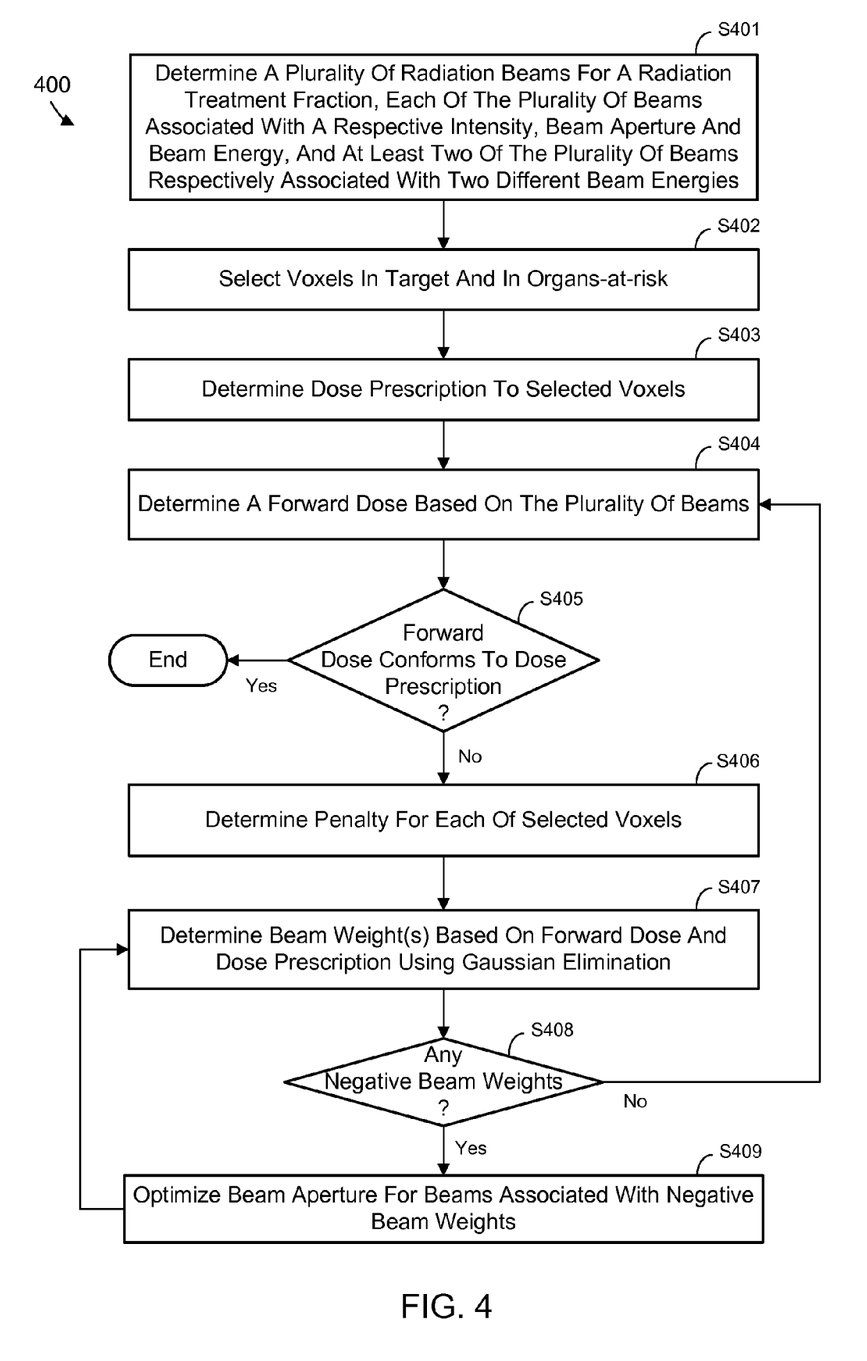
FIG. 4 comprises a flow diagram illustrating a process according to some embodiments.

FIG. 4 is a flow diagram of a process to generate a mixed-energy IMRT plan according to some embodiments. Process 400 and the other processes described herein may be performed using any suitable combination of hardware, software or manual means. Software embodying these processes may be stored by any medium, including a fixed disk, a floppy disk, a CD-ROM, a DVD-ROM, a Zip™ disk, a magnetic tape, or a signal. Examples of these processes will be described below with respect to the elements of treatment room 100, but embodiments are not limited thereto.

Generally, process 400 includes determination of a plurality of radiation beams for a radiation treatment fraction, where each of the plurality of beams is associated with a respective intensity, beam aperture and beam energy, and at least two of the plurality of beams are respectively associated with two different beam energies. Process 400 also includes determination of a forward dose associated with the plurality of input beams.

Process 400 may be performed after generating a three-dimensional image of a patient volume. Such an image is typically acquired by a computed tomography scanner and allows a treatment planner/oncologist to identify target volumes (e.g., tumors) and surrounding sensitive tissues (e.g., organs-at-risk).

A plurality of radiation beams for a radiation treatment fraction are determined at S401. Each of the plurality of radiation beams is associated with a respective intensity, beam aperture and beam energy, and at least two of the plurality of beams are respectively associated with different beam energies.

The selection of beam intensities and apertures, as well as gantry angles, for treating a given tumor is known in the field of IMRT. The present inventors have discovered that beam energy provides an additional degree of freedom for varying the dose profile along an axis of a beam. For example, high-energy photons (e.g., 10-21 MV) may be suited for treating a tumor that is deep-seated (e.g., >20 cm from the skin surface) at a particular entry point, while lower-energy photons (4-6 MV) may be suitable for treating the same tumor through an entry point at which the tumor is only 5 cm from the skin surface.

Figure 5:
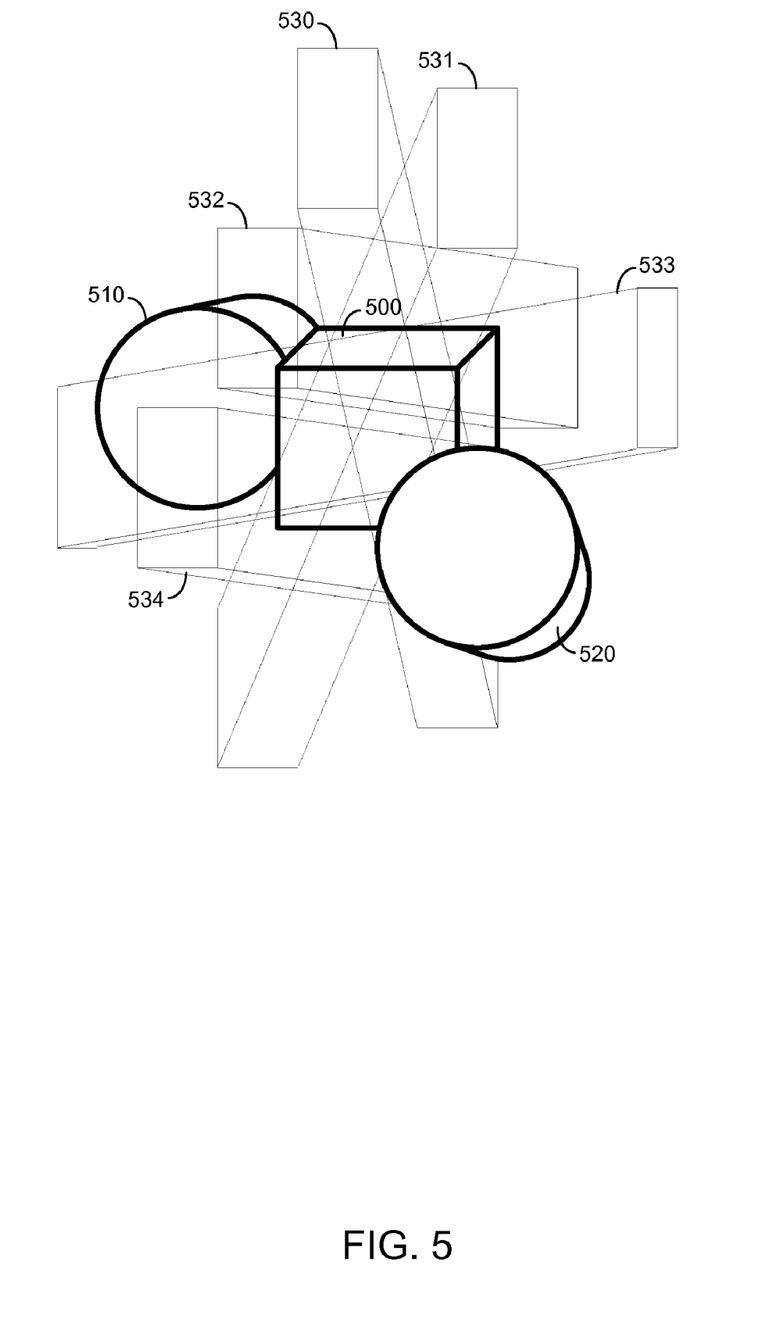
FIG. 5 illustrates beam shapes and angles of a treatment fraction according to some embodiments.

FIG. 5 is a simplified diagram illustrating the determination of a plurality of radiation beams according to some embodiments of S401. Shape 500 represents a target volume in a three-dimensional image of a patient volume. Shapes 510 and 520 illustrate organs-at-risk. Beams 530-534 have been determined manually and/or automatically using treatment planning software. Each of beams 530-534 is associated with a different gantry (i.e., entry) angle. Each of beams 530-534 may be associated with a different aperture, intensity and/or energy. The sizes and shapes of each aperture may differ, despite the depiction of similar aperture shapes in FIG. 5. These parameters are initially selected with the intention of providing a suitable dose to shape 500 while not exceeding a maximum dose to shapes 510 and 520.

Voxels in the target and the organs-at-risk are selected at S402. Voxel sampling is a known process for selecting some fraction of voxels for which a forward dose will be calculated. Any fraction of the total voxels may be selected at S402. In some embodiments, less than 200 voxels are selected at S402.

A dose prescription to the selected voxels is determined at S403. In some embodiments, a dose prescription for an entire patient volume is determined prior to process 400 and S403 comprises determining the dose prescription to the selected voxels based on the dose prescription for the entire patient volume. Alternatively, the dose prescription for each voxel may be independently determined.

Next, at S404, a forward dose is determined based on the plurality of beams using known algorithms. For example, S404 may comprise a determination such as set forth in *Bedford, "Speed versus accuracy in a fast convolution photon dose calculation for conformal radiotherapy," Phys. Med. Biol.* 47, 3475-3484 (2002)

At S405, it is determined whether the forward dose conforms to the dose prescription determined at S403. Some embodiments of S405 include determining the forward dose determined for each selected voxel with its associated dose prescription. Process 400 terminates if it is determined that the forward dose conforms to the dose prescription.

In contrast, flow proceeds to S406 if it is determined that the forward dose does not conform to the dose prescription. At S406, a penalty for each of a plurality of selected voxels is determined.

According to some embodiments, the penalties P, for the target volume are determined at 406 as:

$$(_{max}P_{ptv})/MD_i > D_{p,max}$$

$$P_i = 0 \; D_{p,min}$$

$$(_{min}P_{ptv})/MD_i < D_{p,min}, \text{ where } M \text{ is the number of voxels in the volume.}$$

For organs-at-risk, only overdosage penalties are determined as:

$$P_{oar}/M \, D_i > D_p(l)$$

$P_i=0 \, D_i <= D_p(l)$, where $M$ is the number of voxels in the volume.

Next, at S407, a weight is determined for each of the plurality of beams based on the determined forward dose, the dose prescription and the penalties for the selected voxels. The beam weights are determined in some embodiments by solving the following equation:

$$\sum_{i=1}^{N} P_i(D_i(x) - {}^P D_i)^2,$$

where N is the number of selected voxels, $D_i=D_i(x)$ and ${}^P D_i$ are the determined forward dose and the prescribed maximum dose in voxel and the array x contains the beam parameters. The prescribed maximum dose for the target volume may be segmented into limits for overdosage ($D_{p,max}$) and for underdosage ($D_{p,min}$). The array $P_i$ includes the penalties.

In order to solve the equation shown above, a system of linear equations is generated at S407 as follows:

$$D_{11}W_1 + D_{12}W_2 + \ldots D_{1n}W_n = d_1$$

$$D_{21}W_1 + D_{22}W_2 + \ldots D_{2n}W_n = d_2$$

$$D_{m1}W_1 + D_{m2}W_2 + \ldots D_{mn}W_n = d_m,$$

where $D_{mn}$ is the dose to an $n^{th}$ voxel from an $m^{th}$ beam segment before optimization and $W_1, W_2 \ldots W_n$ are the beam weights needed to produce a prescribed dose of $d_m$ at the selected voxel. Again, Gaussian elimination may be applied to the above system of linear equations to determine the beam weights $W_1, W_2 \ldots W_n$. Examples of such Gaussian elimination for solving a system of linear equations may be found in Chawla, "*A parallel Gaussian elimination method for general linear systems, International Journal of Computer Mathematics*", 42, 1029-0265 (1992), *and* Grimes, "*Solving Systems of Large Dense Linear Equations,*" *The Journal of Supercomputing*, 1, 291-299 (1988).

At S408, it is determined whether any of the determined beam weights are negative. If not, flow returns to S404 to determine a forward dose based on the plurality of beams and their respective weights determined at S407. Flow then proceeds as described above.

If one or more of the determined beam weights are negative, the beam aperture of each beam associated with a negative beam weight is optimized at S409. In this regard, a negative beam weight $W_n$ indicates that the plurality of beams result in too large a dose to the nth voxel. Accordingly, the aperture of one or more beams is changed at S409 to eliminate some or all of the radiation delivered to the voxel. The optimization of S409 may be performed for all voxels associated with a negative beam weight. Flow then returns to S407 and continues as described above.

The output of process 400 is a set of beams and associated apertures, intensities, gantry angles and energies. As described above, these beams may be delivered in a single IMRT fraction. For example, a patient volume is positioned on table 120 with respect to linac 110 according to a treatment plan. Linac 110 then delivers a beam associated with a first aperture, intensity, gantry angle and energy to the patient volume.

Figure 6:
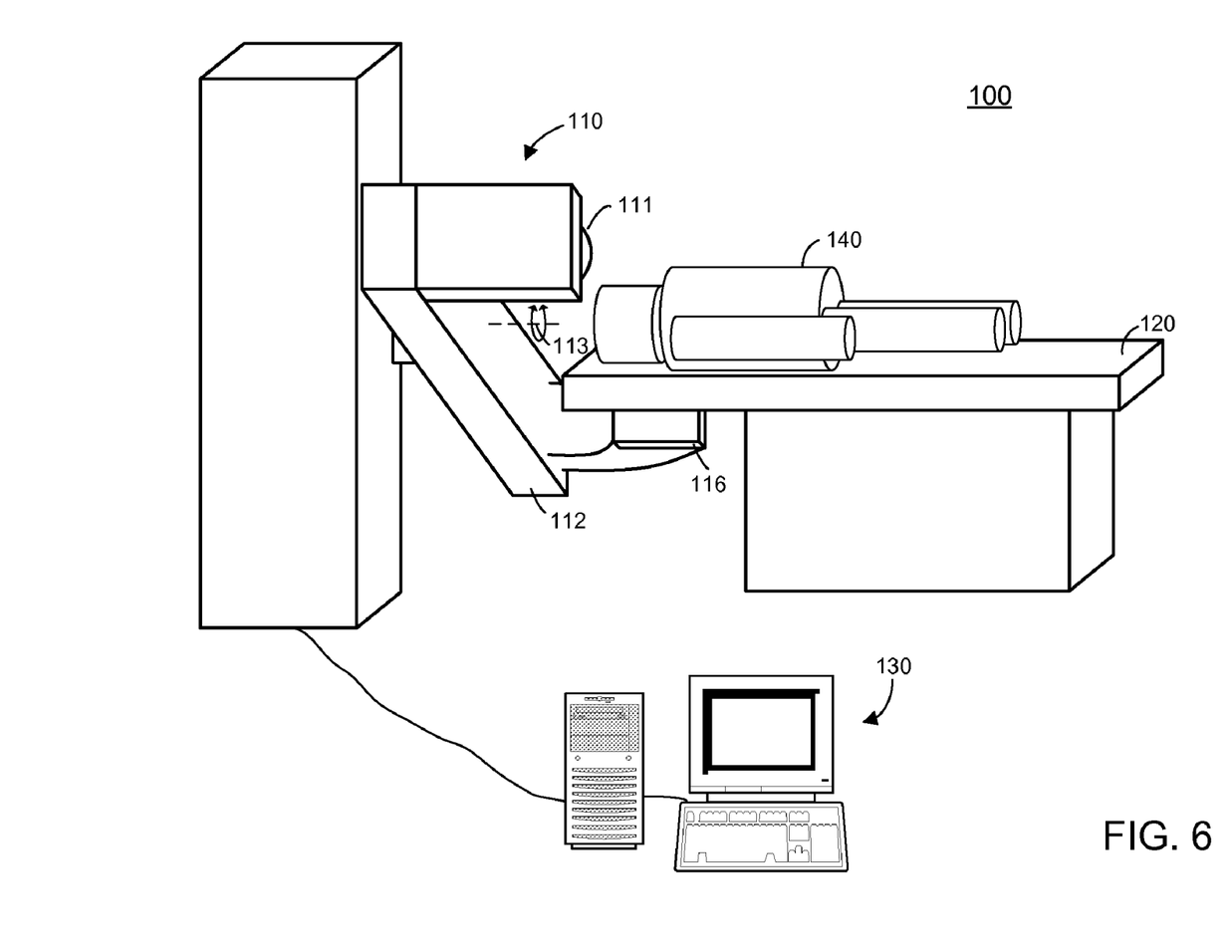
FIG. 6 is a perspective view of a radiation treatment room according to some embodiments.

Linac 110 is then operated to change an energy of a next-emitted radiation beam. Zero or more of the aperture, intensity and gantry angle may also be changed. For example, FIG. 6 shows treatment room 100 with gantry 112 positioned at an angle different from that shown in FIG. 1. A second beam may be delivered to the patient volume from the illustrated gantry angle. The second beam exhibits an energy different from the first beam, and, as mentioned above, may also differ in aperture and/or intensity. Typically, the position of the patient volume is maintained between delivery of the first and second beams.

Embodiments may provide more than two beams per treatment fraction. Each beam is associated with a respective aperture, intensity, gantry angle and energy. Two or more beams may share at least one of a same aperture, intensity, gantry angle or energy.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A method comprising:
    determining, by a processor, a plurality of radiation beams for a radiation treatment fraction, each of the plurality of beams associated with a respective intensity, beam aperture and beam energy, and at least two of the plurality of beams respectively associated with two different beam energies;
    determining, by the processor, a forward dose associated with the plurality of beams;
    determining, by the processor, that the forward dose does not conform to a dose prescription;
    determining, using Gaussian elimination, a beam weight for each of the plurality of beams based on the forward dose and the dose prescription;
    determining, by the processor, that the beam weight for at least one of the plurality of beams is negative;
    changing the at least one beam aperture associated with the at least one of the plurality of beams;
    determining, by the processor, a second beam weight for each of the plurality of beams based on the changed at least one beam aperture; and
    determining, by the processor, a second forward dose associated with the plurality of beams and the second beam weights.

2. A method according to claim 1, further comprising:
    delivering the plurality of beams to a patient volume in a single treatment fraction according to their respective intensity, beam aperture and beam energy.

3. A method according to claim 2, wherein delivering the plurality of beams comprises:
    delivering one of the at least two of the plurality of beams at a first beam energy from a therapeutic radiation source;
    changing a configuration of the therapeutic radiation source to generate beams at a second beam energy; and
    delivering a second one of the at least two of the plurality of beams at the second beam energy from the therapeutic radiation source.

4. A method according to claim 3, wherein the one of the at least two of the plurality of beams is delivered while the patient volume is in a first position, and
    wherein the second one of the at least two of the plurality of beams is delivered while the patient volume is in the first position.

5. A method according to claim 1, wherein the two different beam energies are megavoltage energies.

6. A non-transitory medium having processor-executable program code stored thereon, the medium comprising:
   code to determine a plurality of radiation beams for a radiation treatment fraction, each of the plurality of beams associated with a respective intensity, beam aperture and beam energy, and at least two of the plurality of beams respectively associated with two different beam energies;
   code to determine a forward dose associated with the plurality of beams;
   code to determine that the forward dose does not conform to a dose prescription; determine, using Gaussian elimination, a beam weight for each of the plurality of beams based on the forward dose and the dose prescription;
   code to determine that the beam weight for at least one of the plurality of beams is negative;
   code to change the at least one beam aperture associated with the at least one of the plurality of beams;
   code to determine a second beam weight for each of the plurality of beams based on the changed at least one beam aperture; and
   code to determine a second forward dose associated with the plurality of beams and the second beam weights.

7. A medium according to claim 6, further comprising:
   code to deliver the plurality of beams to a patient volume in a single treatment fraction according to their respective intensity, beam aperture and beam energy.

8. A medium according to claim 7, wherein delivering the plurality of beams comprises:
   delivering one of the at least two of the plurality of beams at a first beam energy from a therapeutic radiation source;
   changing a configuration of the therapeutic radiation source to generate beams at a second beam energy; and
   delivering a second one of the at least two of the plurality of beams at the second beam energy from the therapeutic radiation source.

9. A medium according to according to claim 8, wherein the one of the at least two of the plurality of beams is delivered while the patient volume is in a first position, and wherein the second one of the at least two of the plurality of beams is delivered while the patient volume is in the first position.

10. A medium according to claim 6, wherein the two different beam energies are megavoltage energies.

* * * * *